United States Patent
Hsu et al.

(10) Patent No.: US 8,484,003 B2
(45) Date of Patent: Jul. 9, 2013

(54) METHODS, APPARATUS AND ARTICLES OF MANUFACTURE TO PROCESS MEASUREMENTS OF WIRES VIBRATING IN FLUIDS

(75) Inventors: Kai Hsu, Sugar Land, TX (US); Christopher Harrison, Auburndale, MA (US); Matthew T. Sullivan, Westwood, MA (US); Michael Stangeland, Tokyo (JP); Anthony Smits, Kawasaki (JP); Anthony Robert Holmes Goodwin, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 979 days.

(21) Appl. No.: 12/553,967

(22) Filed: Sep. 3, 2009

(65) Prior Publication Data

US 2010/0241407 A1    Sep. 23, 2010

Related U.S. Application Data (60) Provisional application No. 61/161,391, filed on Mar. 18, 2009.

(51) Int. Cl.
 *G06G 7/48* (2006.01)
(52) U.S. Cl.
 USPC ..................... 703/10; 703/2; 703/6
(58) Field of Classification Search
 USPC .................................. 703/2, 6, 10
 See application file for complete search history.

(56) References Cited

U.S. PATENT DOCUMENTS

| | | | |
|---|---|---|---|
| 7,194,902 B1 | 3/2007 | Goodwin et al. | |
| 7,222,671 B2 | 5/2007 | Caudwell et al. | |
| 7,395,878 B2 | 7/2008 | Reitsma et al. | |
| 7,526,953 B2* | 5/2009 | Goodwin et al. | 73/152.28 |
| 7,574,898 B2 | 8/2009 | Harrison et al. | |
| 7,784,330 B2* | 8/2010 | Angelescu et al. | 73/54.09 |
| 2006/0137873 A1 | 6/2006 | Caudwell et al. | |
| 2006/0243047 A1* | 11/2006 | Terabayashi et al. | 73/152.55 |
| 2007/0263488 A1 | 11/2007 | Clark | |
| 2010/0116550 A1* | 5/2010 | Hutin et al. | 175/40 |
| 2010/0206063 A1* | 8/2010 | Fujisawa et al. | 73/152.24 |

FOREIGN PATENT DOCUMENTS

GB    2421526    6/2006

OTHER PUBLICATIONS

Sullivan et al., "On the Nonlinear Interpretation of a Vibrating Wire Viscometer Operated at a Large Amplitude", Fluid Phase Equilibra 276 (2008), pp. 99-107.

* cited by examiner

*Primary Examiner* — Omar Fernandez Rivas
*Assistant Examiner* — Herng-Der Day
(74) *Attorney, Agent, or Firm* — Jianguang Du; Jody DeStefanis (57) ABSTRACT

Example methods, apparatus and articles of manufacture to process measurements of wires vibrating in fluids are disclosed. A disclosed example apparatus includes a downhole assembly and a surface assembly. The downhole assembly including a sensor to measure a waveform representative of a motion of a wire vibrating within a fluid at a downhole location in a wellbore, a waveform modeler to compute a model parameter from the measured waveform, and a first telemetry module to transmit the computed model parameter to a surface location. The surface assembly including a second telemetry module to receive the computed model parameter from the downhole assembly, and a viscosity analyzer to estimate a viscosity of the fluid from the computed model parameter.

34 Claims, 6 Drawing Sheets

METHODS, APPARATUS AND ARTICLES OF MANUFACTURE TO PROCESS MEASUREMENTS OF WIRES VIBRATING IN FLUIDS

RELATED APPLICATIONS

This patent claims the benefit of U.S. Provisional Patent Application No. 61/161,391, entitled "Two Step Processing of Vibrating Wire Sensor," and filed Mar. 18, 2009, which is hereby incorporated by reference in its entirety.

FIELD OF THE DISCLOSURE

This patent relates generally to wires vibrating in fluids and, more particularly, to methods, apparatus and articles of manufacture to process measurements of wires vibrating in fluids.

BACKGROUND

Wellbores are drilled to, for example, locate and produce hydrocarbons. During a drilling operation, it may be desirable to perform evaluations of the formations penetrated and/or encountered formation fluids. In some cases, a drilling tool is removed and a wireline tool is then deployed into the wellbore to test and/or sample the formation and/or fluids associated with the formation. In other cases, the drilling tool may be provided with devices to test and/or sample the surrounding formation and/or formation fluids without having to remove the drilling tool from the wellbore. These samples or tests may be used, for example, to characterize hydrocarbons extracted from the formation.

Formation evaluation often requires fluid(s) from the formation to be drawn into the downhole tool for testing, evaluation and/or sampling. Various devices, such as probes, are extended from the downhole tool to establish fluid communication with the formation surrounding the wellbore and to draw fluid(s) into the downhole tool. Fluid(s) passing through and/or captured within the downhole tool may be tested and/or analyzed to determine various parameters and/or properties while the downhole tool is positioned in situ, that is, within a wellbore. Various properties of hydrocarbon reservoir fluids, such as viscosity, density and phase behavior of the fluid at reservoir conditions may be used to evaluate potential reserves, determine flow in porous media and design completion, separation, treating, and metering systems, among others.

SUMMARY

Example methods, apparatus and articles of manufacture to process measurements of wires vibrating in fluids are disclosed. A disclosed example apparatus includes a downhole assembly and a surface assembly. The downhole assembly including a sensor to measure a waveform representative of a motion of a wire vibrating in a flow of a fluid at a downhole location in a wellbore, a waveform modeler to compute a model parameter from the measured waveform, and a first telemetry module to transmit the computed model parameter to a surface location. The surface assembly including a second telemetry module to receive the computed model parameter from the downhole assembly, and a viscosity analyzer to estimate a viscosity of the fluid from the computed model parameter.

A disclosed example method includes actuating a wire sensor within a fluid, measuring a waveform representative of a vibration of the wire sensor within the fluid, computing a wire vibration model parameter comprising at least one of a resonant frequency or a logarithmic decrement damping factor from the measured waveform, and estimating a viscosity of the fluid from the computed model parameter.

A disclosed example apparatus for use at a downhole location of a wellbore includes an actuator to actuate a wire within a fluid at the downhole location of the wellbore, a measurer to measure a waveform representative of a vibration of the wire within the fluid, a transformer to compute a Hilbert transform of the measured waveform and to compute a target waveform based on the Hilbert transform and the measured waveform, a decrement fitter to select first and second coefficients of a linear model to reduce a difference between the linear model and the computed target waveform and to compute a logarithmic decrement damping factor based on the first coefficient, and a telemetry module to send the computed logarithmic decrement damping factor to a surface location.

Another disclosed example method includes actuating a wire within a fluid at a downhole location within a wellbore, measuring a waveform representative of a vibration of the wire within the fluid, computing a Hilbert transform of the measured waveform, computing a target waveform based on the Hilbert transform and the measured waveform, selecting first and second coefficients of a linear model to reduce a difference between the linear model and the computed target waveform, computing a logarithmic decrement damping factor based on the first coefficient, and sending the computed logarithmic decrement damping factor to a surface location.

Yet another disclosed example method includes receiving at a surface location a logarithmic decrement damping factor for a wire vibrating within a fluid at a downhole location within a wellbore, receiving at the surface location from the downhole location a resonant frequency of the vibrating wire within the fluid within the wellbore at the downhole location, and estimating a viscosity of the fluid based on the received logarithmic decrement damping factor and the received resonant frequency.

Certain examples are shown in the above-identified figures and described in detail below. In describing these examples, like or identical reference numbers may be used to identify common or similar elements. The figures are not necessarily to scale and certain features and certain views of the figures may be shown exaggerated in scale or in schematic for clarity and/or conciseness. Moreover, while certain preferred embodiments are disclosed herein, other embodiments may be utilized and structural changes may be made without departing from the scope of the invention.

DETAILED DESCRIPTION

The example methods, apparatus and articles of manufacture disclosed herein provide certain advantages for formation evaluation. Given the density $\rho$ of a fluid, the viscosity $\eta$ of the fluid can be estimated using a vibrating wire sensor. Traditionally, measurements of the vibrations of the wire sensor are transmitted from a downhole tool at a downhole location to a surface location for subsequent processing at the surface to estimate fluid viscosity $\eta$. However, the telemetry transmission bandwidth needed to transmit the measurements from the downhole location to the surface location may exceed the available bandwidth, which may prevent real-time determination of fluid viscosities during formation evaluation.

To overcome these difficulties, the examples described herein process the measurements of the wire sensor vibrations in two phases. In a first phase, which can be implemented using the processing and/or computing resources ordinarily and/or readily available in a downhole tool, a resonant frequency $\omega$ and a logarithmic decrement damping factor $\Delta$ that characterize and/or represent the vibrations of the wire sensor are computed from the measurements. The computed model parameters, that is, the computed resonant frequency $\omega$ and the logarithmic decrement damping factor $\Delta$, are transmitted from the downhole tool to a surface location using only a fraction of the telemetry bandwidth required to send the measurements themselves to the surface location. In a second phase, at the surface location where more computing resources are readily available, the computed model parameters $\omega$ and $\Delta$ are combined with one or more calibration parameters to define a fluid viscosity modeling equation g( ), which is iterated to estimate and/or solve for the viscosity $\eta$ of the fluid in which the vibrations of the wire sensor were measured. Because the computational burden on the downhole tool and the telemetry bandwidth requirements are reduced, the examples described herein enable substantially real-time determination of formation fluid viscosity $\eta$ as formation evaluation proceeds.

Figure 1:
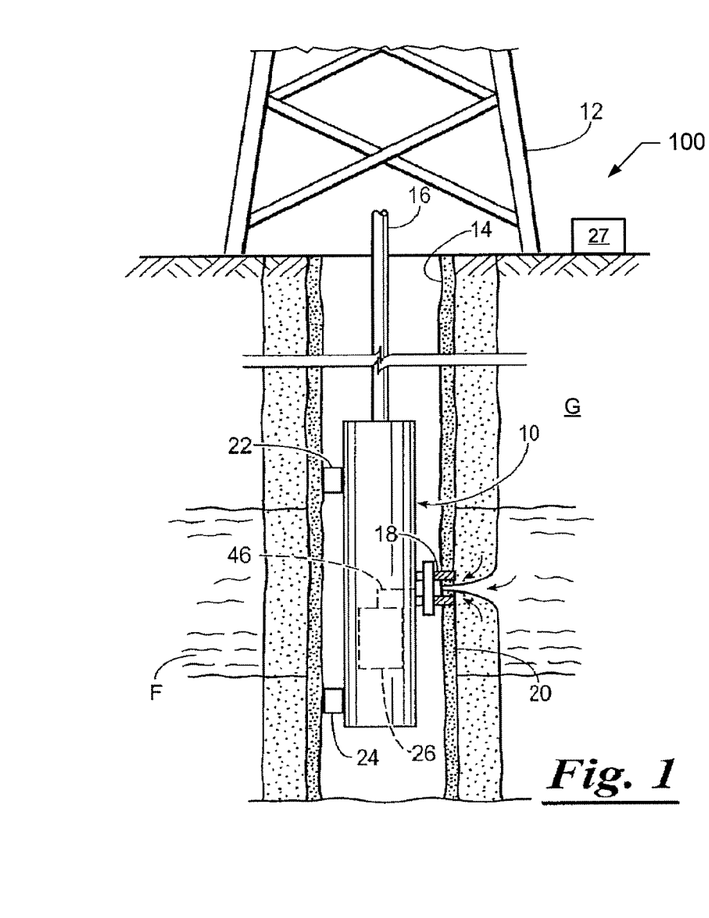
FIGS. 1 and 2 are schematic, partial cross-sectional views of example formation evaluation apparatus having a downhole fluid viscosity analysis assembly and a surface fluid viscosity analysis assembly to process measurements of wires vibrating in fluid flows.

FIG. 1 shows a schematic, partial cross-sectional view of an example formation evaluation apparatus 100. In the illustrated example of FIG. 1, a downhole tool 10 of FIG. 1 is suspended from a rig 12 in a wellbore 14 formed in a geologic formation G. The example downhole tool 10 can implement any type of downhole tool capable of performing formation evaluation, such as fluorescence, formation fluid analysis, formation fluid sampling, well logging, etc. The example downhole tool 10 of FIG. 1 is a wireline tool deployed from the rig 12 into the wellbore 14 via a wireline cable 16 and positioned adjacent to a particular portion F of the geologic formation G.

To seal the example downhole tool 10 of FIG. 1 to a wall 20 of the wellbore 14 (hereinafter referred to as a "wall 20" or "wellbore wall 20"), the example downhole tool 10 includes a probe 18. The example probe 18 of FIG. 1 forms a seal against the wall 20 and draws fluid(s) from the formation F into the downhole tool 10 as depicted by the arrows. Backup pistons 22 and 24 assist in pushing the example probe 18 of the downhole tool 10 against the wellbore wall 20.

To perform fluid viscosity analysis, the example formation evaluation apparatus 100 of FIG. 1 includes a downhole fluid viscosity analysis assembly 26 and a surface fluid viscosity analysis assembly 27 constructed in accordance with the teachings of this disclosure. The example downhole assembly 26 receives formation fluid(s) from the probe 18 via an evaluation flowline 46. The example downhole fluid viscosity analysis assembly 26 of FIG. 1 measures that electromotive force (emf) D(t), which is a voltage that develops and/or is induced as a result of temporal changes of the magnetic flux passing through a loop partially defined by the location(s), displacement(s), movement(s) and/or vibration(s) of a wire as it vibrates within a fluid contained in and/or flowing in the flowline 46. The example downhole assembly 26 computes a resonant frequency $\omega$ and a logarithmic decrement damping factor $\Delta$ that are characteristic and/or representative of the measured emf D(t), and transmits the computed model parameters $\omega$ and $\Delta$ to the surface assembly 27 using any number and/or type(s) of telemetry and/or data transmission(s). In some examples, the downhole assembly 26 computes an estimate and/or approximation of the viscosity $\eta$ of the fluid from the computed log decrement $\Delta$ to facilitate other formation evaluations performed by the downhole tool 10. For example, the downhole assembly 26 can estimate the viscosity $\eta$ as a constant times the square of the decrement $\Delta$. The downhole tool 10 can compare such an estimate of the viscosity $\eta$ to a threshold to, for example, determine a fluid draw down rate for a formation evaluation test. An example manner of implementing the example downhole assembly fluid viscosity analysis 26 of FIG. 1 is described below in connection with FIG. 3.

The example surface fluid viscosity analysis assembly 27 of FIG. 1 receives the computed model parameters $\omega$ and $\Delta$ from the downhole assembly 26 and combines them with one or more calibration parameters to define the viscosity modeling equation g( ). The surface assembly 27 iteratively computes outputs of the viscosity modeling equation g( ) to estimate and/or solve for the viscosity $\eta$ of the fluid within the flowline 46. In some examples, the example surface fluid viscosity analysis assembly 27 may additionally or alternatively receive from the downhole assembly 26 an estimate of the viscosity $\eta$, which may be computed as described above. The viscosity $\eta$ received from the downhole assembly 26 may be used by the example surface assembly 27 as an initial starting point $\eta_0$ for iterations of the viscosity modeling equation g( ). An example manner of implementing the example surface assembly fluid viscosity analysis 27 of FIG. 1 is described below in connection with FIG. 4.

Figure 2:
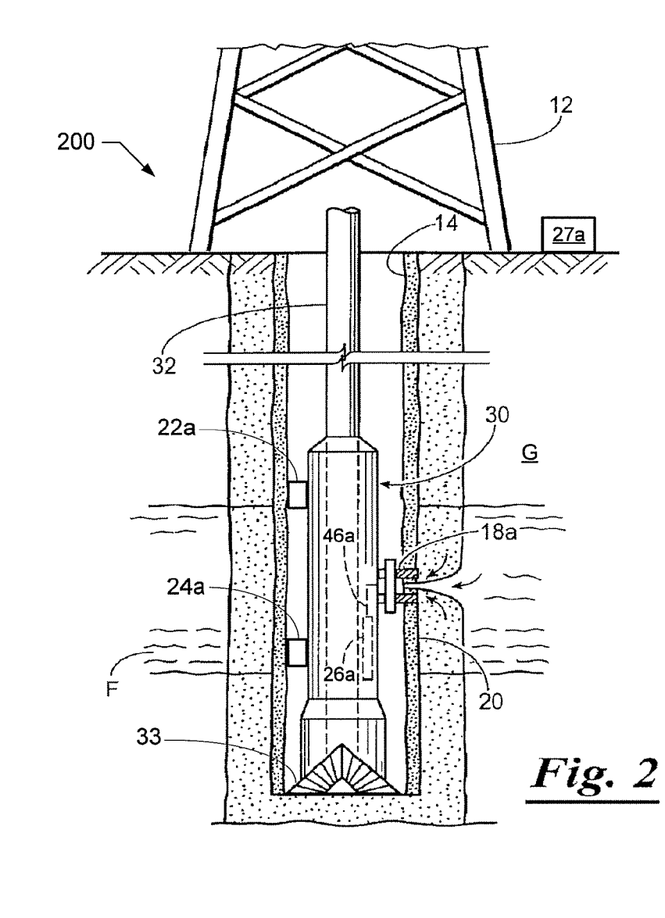

FIG. 2 shows a schematic, partial cross-sectional view of another example formation evaluation apparatus 200. In the illustrated example of FIG. 2, a downhole tool 30 is attached to a drillstring 32 and a drill bit 33 driven by the rig 12 and/or a mud motor (not shown) driven by mud flow to form the wellbore 14 in the geologic formation G. The example downhole tool 30 of FIG. 2 is conveyed among one or more of (or itself may be) a measurement-while-drilling (MWD) tool, a logging-while-drilling (LWD) tool, or other type of downhole tool that are known to those skilled in the art.

To seal the example downhole tool 30 of FIG. 2 to the wall 20 of the wellbore 14, the downhole tool 30 includes a probe 18a. The example probe 18a of FIG. 2 forms a seal against the wall 20 to draw fluid(s) from the formation F into the downhole tool 30 as depicted by the arrows. Backup pistons 22a and 24a assist in pushing the example probe 18a of the downhole tool 30 against the wellbore wall 20. Drilling is stopped before the probe 18a is brought in contact with the wall 20.

To perform fluid viscosity analysis, the example formation evaluation apparatus 200 of FIG. 2 includes a downhole fluid viscosity analysis assembly 26a and a surface fluid viscosity analysis assembly 27a constructed in accordance with the teachings of this disclosure. The example downhole assembly 26a receives formation fluid(s) from the probe 18a via an evaluation flowline 46a. The example downhole fluid viscosity analysis assembly 26a of FIG. 2 measures that emf D(t), which is a voltage that develops and/or is induced as a result of temporal changes of the magnetic flux passing through a loop partially defined by the location(s), displacement(s), movement(s) and/or vibration(s) of the wire as it vibrates within a fluid contained in and/or flowing in the flowline 46a. The example downhole assembly 26a computes a resonant frequency ω and a logarithmic decrement damping factor Δ that are characteristic and/or representative of the measured emf D(t), and transmits the computed model parameters ω and Δ to the surface assembly 27a using any number and/or type(s) of telemetry and/or data transmission(s). In some examples, the downhole assembly 26a computes an estimate and/or approximation of the viscosity η of the fluid from the computed log decrement Δ to facilitate other formation evaluations performed by the downhole tool 30. For example, the downhole assembly 26a can estimate the viscosity as a constant times the square of the decrement Δ. The downhole tool 30 can compare such an estimate of the viscosity η to a threshold to, for example, determine a fluid draw down rate for a formation evaluation test. An example manner of implementing the example downhole assembly fluid viscosity analysis 26a of FIG. 2 is described below in connection with FIG. 3.

The example surface fluid viscosity analysis assembly 27a of FIG. 2 receives the computed model parameters ω and Δ from the downhole assembly 26a and combines them with one or more calibration parameters to define the viscosity modeling equation g( ). The surface assembly 27a iteratively computes outputs of the viscosity model equation g( ) to estimate and/or solve for the viscosity η of the fluid within the flowline 46a. In some examples, the example surface fluid viscosity analysis assembly 27a may additionally or alternatively receive from the downhole assembly 26a an estimate of the viscosity η, which may be computed as described above. The viscosity η received from the downhole assembly 26a may be used by the example surface assembly 27a as an initial starting point $\eta_0$ for iterations of the viscosity modeling equation g( ). An example manner of implementing the example surface assembly fluid viscosity analysis 27a of FIG. 2 is described below in connection with FIG. 4.

Figure 3:
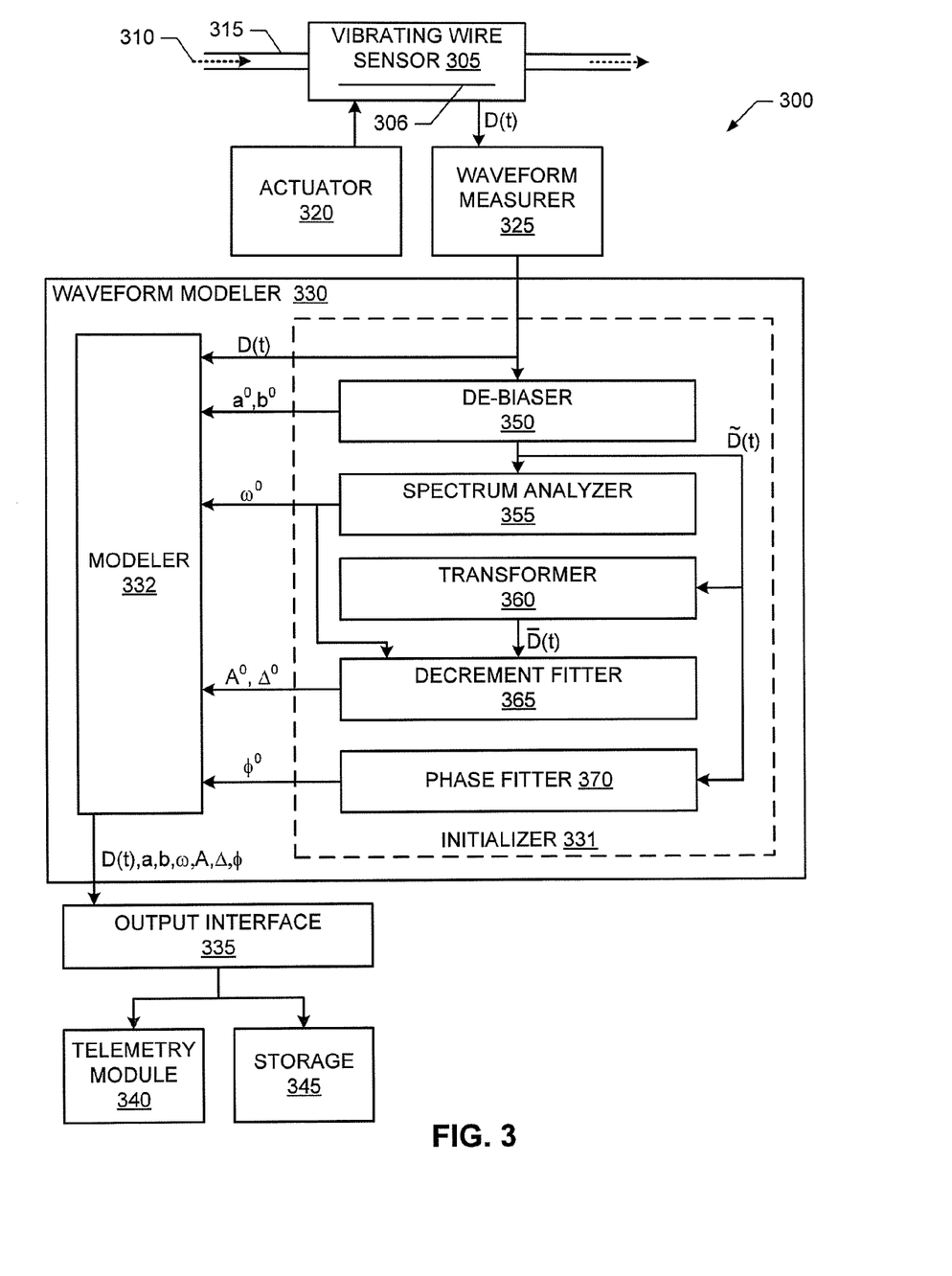
FIG. 3 illustrates an example manner of implementing the example downhole fluid viscosity analysis assemblies of FIGS. 1 and 2.

FIG. 3 illustrates an example manner of implementing the example downhole fluid viscosity analysis assemblies 26 and 26a of FIGS. 1 and 2. While either of the example downhole fluid viscosity analysis assemblies 26 and 26a may be implemented by the example of FIG. 3, for ease of discussion, the illustrated example of FIG. 3 will be referred to as downhole fluid viscosity analysis assembly 300, or simply as downhole assembly 300.

To take measurements representative of a viscosity η of a fluid 310 flowing in a flowline 315, the example downhole assembly 300 of FIG. 3 includes any type of vibrating wire sensor 305, any type of actuator 320 and any type of waveform measurer 325. The example vibrating wire sensor 305 of FIG. 3 includes a wire 306 held in tension within the flowline 315. The example actuator 320 of FIG. 3 includes any number and/or type(s) of electromagnetic source(s) and magnets to actuate, activate and/or induce displacement(s) of the wire 306 within the wire sensor 305. The example waveform measurer 325 of FIG. 3 measures an induced emf voltage D(t) developed across the wire 306 in response to the actuator 320 and that depends on the viscosity η of the fluid 310. While in practice the waveform measurer 325 outputs digital samples representative of the induced emf voltage D(t), for ease of discussion, the output of the waveform measurer 325 will be referred to herein as D(t). The induced emf voltage D(t) represents a waveform characteristic and/or representative of the motion of the wire 306 over time.

Example vibrating wire sensors 305, actuators 320 and waveform measurers 325 are described in U.S. Pat. No. 7,574,898, entitled "Vibrating Wire Viscosity Sensor," and granted Aug. 18, 2009; U.S. patent application Ser. No. 12/534,151, entitled "Vibrating Wire Viscometers," and filed Aug. 2, 2009; U.S. patent application Ser. No. 12/537,257, entitled "Vibrating Wire Viscometers," and filed Aug. 7, 2009; U.S. Pat. No. 7,194,902, entitled "Apparatus and Method for Formation Evaluation, and granted Mar. 27, 2007; and U.S. Pat. No. 7,222,671, entitled "Apparatus and Method for Formation Evaluation, and granted May 29, 2007, all of which are assigned to the assignee of the present patent, and all of which are incorporated herein by reference in their entireties. Example methods to process the induced emf voltage waveform D(t) to estimate the viscosity η of the fluid 310 are described in a paper entitled "On the Nonlinear Interpretation of a Vibrating Wire Viscometer Operated at a Large Amplitude," authored by Sullivan et al., and appearing in Fluid Phase Equilibra 276 (2008), pp. 99-107, which was authored at least in part by inventors of the present patent, and which is incorporated herein by reference in its entirety.

In the transient mode, the induced emf voltage D(t) developed across the wire 306 in the presence of the fluid 310 is a short-lived oscillation that conforms to a simple damped harmonic model, which can be expressed mathematically as $$V(t) = A e^{-\Delta \omega t} \sin(\omega t + \phi), \qquad \text{EQN (1)}$$

where V(t) is an estimate of the measured induced emf voltage D(t), where A is the amplitude of the initial transient, Δ is a logarithmic decrement damping factor that controls the damping of the motion, ω is the resonance frequency of the wire 306 (in radian/sec), t is the time index, and φ is an unknown phase angle.

The logarithmic decrement Δ of EQN (1) is related to properties of the fluid 310 and to properties of the wire 306. The logarithmic decrement Δ can be expressed mathematically as $$\Delta = \frac{(\rho/\rho_s)k' + 2\Delta_0}{2[1 + (\rho/\rho_s)k]}, \qquad \text{EQN (2)}$$

where ρ and $\rho_s$ are the densities of the fluid 310 and the wire 306, respectively, and $\Delta_0$ is the internal damping of the wire 306 in a vacuum. The quantities k and k' of EQN (2) are defined by the mathematical expressions $$k = -1 + 2\Im(\Lambda) \qquad \text{EQN (3)}$$

$$k' = 2\Re(\Lambda) + 2\Delta\Im(\Lambda), \qquad \text{EQN (4)}$$

where $\Im(\ )$ denotes taking the imaginary part of a complex-value quantity, and $\Re(\ )$ denotes taking the real part of a complex-value quantity. In EQNS (3) and (4), the complex-valued quantity Λ is defined by $$\Lambda = (i-\Delta)\left[1 + \frac{2K_1\left[((i-\Delta)\Omega)^{\frac{1}{2}}\right]}{[(i-\Delta)\Omega]^{\frac{1}{2}}K_0\left[((i-\Delta)\Omega)^{\frac{1}{2}}\right]}\right], \quad \text{EQN (5)}$$

where $$\Omega = \frac{\omega\rho R^2}{\eta}. \quad \text{EQN (6)}$$

$K_0$ and $K_1$ of EQNS (5) and (6) are modified Bessel functions of the second kind, and $\Omega$ is related to the Reynolds number that characterizes the flow around the cylindrical wire 306 of radius R. In EQN (6), the fluid viscosity and density of the fluid 310 are given by $\eta$ and $\rho$, respectively.

In practice, due to the electrical impedance of the stationary wire 306, an unknown background drift may be present in the induced emf voltage D(t), which can be accounted for with the following mathematical expression:

$$V(t) = Ae^{-\Delta\omega t}\sin(\omega t+\phi)+a+bt, \quad \text{EQN (7)}$$

where a and b are unknown constants that characterize the offset and time-drift due to the unknown background interference.

For excitation of the wire 306 using a large voltage and/or at a large displacement, the mathematical expression of EQN (7) can be enhanced to include a correcting second exponential term, as shown in the following mathematical expression $$V(t) = Ae^{-\Delta\omega t}\sin(\omega t+\phi)+A_3 e^{-3\Delta\omega t}\sin(\omega t+\phi_3)+a+bt. \quad \text{EQN (8)}$$

The mathematical model of EQN (8) is known in the industry as the "VEZA" model. Herein, EQN (7) will be referred to as the single-exponent model and EQN (8) will be referred to as the dual-exponent model. While for the purposes of clarity, the EQNS (1)-(8) assume the fluid 310 is a Newtonian fluid, the example methods and apparatus described herein may, additionally or alternatively, be used to determine the viscosity $\eta$ of non-Newtonian fluids using mathematical models suitable for non-Newtonian fluids. The dual-exponent model of EQN (8) may be used when the wire 306 is oscillated with an amplitude greater than EQNS (1) and (7) can accurately represent. Such conditions may occur, for example, when the drive current and/or magnetic field and, thus, the displacement force applied to the wire 306 are excessive for the damping provided by the surrounding fluid 310. Alternatively, the excessive amplitude can be identified and the ac current applied to the wire 306 reduced and/or if the sensor 305 includes an electromagnet the generated magnetic field may be reduced by reducing the dc power dissipated therein. As the damping provided by the fluid 310 increases the induced emf voltage decreases and, to maintain an acceptable signal-to-noise-ratio, either an increased ac current may be passed through the wire 310 and/or an increased magnetic field may be applied.

To compute one or more model parameters representative and/or characteristic of the measured emf voltage waveform D(t), the example downhole fluid viscosity analysis assembly 300 of FIG. 3 includes a waveform modeler 330. The example waveform modeler 330 of FIG. 3 fits the measured induced emf voltage D(t) (as a function of time) to an expected V(t) as defined by the mathematical expression of EQN (7) to determine, compute and/or otherwise solve for one or more model parameters A, Δ, ω=2πf, $\phi$, a, and b. As described in more detail below, an initializer 331 computes and/or determines initial estimates $A^0$, $\Delta^0$, $\omega^0$, $\phi^0$, $a^0$, and $b^0$ of the model parameters A, Δ, ω, $\phi$, a, and b.

To compute the model parameters A, Δ, ω, $\phi$, a, and b, the example waveform modeler 330 includes a modeler 332. Starting with the initial estimates $A^0$, $\Delta^0$, $\omega^0$, $\phi^0$, $a^0$, and $b^0$ computed by the initializer 331, and using any number and/or type(s) of method(s), equation (s) and/or algorithm(s), the modeler 330 iterate the model parameters A, Δ, ω, $\phi$, a, and b to reduce a difference between the measured emf voltage D(t) and the example V(t) of EQN (7). In some examples, the fitting of the modeled emf voltage V(t) to D(t) is achieved by performing Levenberg-Marquardt iterations to minimize and/or reduce the chi-squared $\chi^2$ between V(t) and D(t), which can be expressed mathematically as $$\min_{A,\Delta,\omega,\phi,a,b} \chi^2, \quad \text{EQN (9)}$$

where $$\chi^2 = \frac{\sum_{i=1}^{N}|D(t_i)-V(t_i)|^2}{\nu}, \quad \text{EQN (10)}$$

$t_i$ represents the times at which samples of the induced emf voltage D(t) were measured by the waveform measurer 325, N is the number of samples being processed, and $\nu$ is the number of degrees of freedom for fitting N data points. An example method of performing Levenberg-Marquardt iterations to solve the mathematically expressions of EQNS (9) and (10) is described by Bevington et al., in a book entitled "Data Reduction and Error Analysis for the Physical Sciences," which is hereby incorporated by reference in its entirety. Additionally and/or alternatively, Newton and/or quasi-Newton iterations may be performed to minimize a difference between the predicted emf voltage V(t) and the measured emf voltage D(t).

The mathematical expressions of EQNS (9) and (10) can be solved without computing values of EQNS (2)-(6). Thus, the model parameters A, Δ, ω, $\phi$, a, and b can be computed by the waveform modeler 330 without having to compute the values of the Bessel functions $K_0$ and $K_1$, which are computational burdensome for the processor of a downhole tool 10, 30 to compute with sufficient accuracy.

For the example dual-exponent model of EQN (8), the example modeler 332 of FIG. 3 reduces and/or minimizes the difference between the measured emf voltage waveform D(t) and the expected waveform V(t) of EQN (8) by, for example, implementing the EQNS (9) and (10) over parameters $A_3$, $\phi_3$, A, Δ, ω, $\phi$, a, and b, where the initial values of $A^3$ and $\phi^3$ are $A_3^0=A^0$ and $\phi_3^0=\phi^0$, respectively.

To output the computed model parameters, the example downhole assembly 300 of FIG. 3 includes any number and/or type(s) of output interface(s), one of which is designated at reference numeral 335. The example output interface 335 of FIG. 3 sends some or all of the computed model parameters (e.g., Δ and ω) and/or the measured waveform D(t) to the surface fluid viscosity analysis assembly 27, 27a via any type of telemetry and/or data transmission module 340, and/or may store the computed model parameters and/or the measured waveform D(t) in any number and/or type(s) of memory(-ies), memory device(s), storage and/or storage device(s) 345.

In some examples, the model parameters are computed during each telemetry frame interval, and sent to the surface fluid viscosity analysis assembly 27, 27a in each telemetry frame. For development and/or testing purposes, periodic and/or aperiodic portions of the measured waveforms D(t) may be split into multiple segments and transmitted to the surface location using multiple telemetry frames.

To remove any bias and/or offset present in the measured waveform D(t), the example initializer 331 of FIG. 3 includes de-biaser 350. The example de-biaser 350 of FIG. 3 computes the average $a^0$ of the measured voltage D(t), and subtracts the average $a^0$ from the measured D(t) to form a zero-mean waveform $\tilde{D}(t)$. That is, $$\tilde{D}(t)=D(t)-a^0. \quad \text{EQN (11)}$$

The example de-biaser 350 sets the initial estimate $b^0$ of b to zero.

To compute an initial estimate $\omega^0$ of the resonant frequency w of the vibrating wire 306, the example initializer 331 of FIG. 3 includes a spectrum analyzer 355. The example spectrum analyzer 355 of FIG. 3 computes a power spectrum of the zero-mean waveform $\tilde{D}(t)$ using, for example, the well-known Welch method. The example spectrum analyzer 355 identifies and/or locates the frequency $f_p$ corresponding to the largest magnitude of the computed power spectrum and computes the resonant frequency $$\omega^0=2\pi f_p.$$

To compute an initial estimate $\Delta^0$ of the logarithmic decrement $\Delta$, the example initializer 331 of FIG. 3 includes a transformer 360 and a decrement fitter 365. The example transformer 360 of FIG. 3 computes the Hilbert transform $\hat{D}(t)$ of the zero-mean waveform $\tilde{D}(t)$. The example transformer 360 computes a target waveform $\overline{D}(t)$ based on the Hilbert transform $\hat{D}(t)$ and the zero-mean waveform $\tilde{D}(t)$. The target waveform $\overline{D}(t)$ is computed using the following mathematical expression $$\overline{D}(t)=\ln(\sqrt{\tilde{D}(t)^2+\hat{D}(t)^2}), \quad \text{EQN (12)}$$

where ln is the natural logarithm, that is the log of base e.

The example decrement fitter 365 of FIG. 3 computes, estimates and/or otherwise solves for an initial estimate $\Delta^0$ of the logarithmic decrement $\Delta$ by fitting a linear model c−dt to the computed target waveform $\overline{D}(t)$. The example decrement fitter 365 solves for the unknowns c and d that minimize the squared difference between the linear model and the target waveform $\overline{D}(t)$. In some examples, the decrement fitter 365 uses a least-squares criterion that can be expressed mathematically as $$\min_{c,d} \sum_{i=1}^{N} |\overline{D}(t_i) - c + dt_i|^2. \quad \text{EQN (13)}$$

The example decrement fitter 365 computes the initial estimated logarithmic decrement $\Delta^0$ and amplitude $A^0$ from the solved for parameters c and d. In particular, the decrement fitter 365 computes:

$$A^0=e^c, \text{ and} \quad \text{EQN (14)}$$

$$\Delta^0=d/\omega^0, \quad \text{EQN (15)}$$

where e is the base of the natural logarithm.

To determine an initial estimate $\phi^0$ of the phase $\phi$, the example initializer 331 includes a phase fitter 370. For each of a plurality of possible phases $\theta$ (e.g., selected from the set {0, $\pi/8, \pi/4, \ldots, 2\pi$}) the example phase fitter 370 of FIG. 3 computes a waveform $\check{D}(t,\theta)$, which can be expressed mathematically as $$\check{D}(t,\theta)=A^0 e^{-\Delta^0 \omega^0 t} \sin(\omega^0 t+\theta). \quad \text{EQN (16)}$$

The example phase fitter 370 computes the mean squared difference between each of the computed waveforms $\check{D}(t,\theta)$ and the zero-mean measured waveform $\tilde{D}(t)$, and selects as the phase $\phi^0$ the phase $\theta$ corresponding to the smallest mean squared difference.

While an example manner of implementing the example downhole fluid viscosity analysis assemblies 26 and 26a of FIGS. 1 and 2 has been illustrated in FIG. 3, one or more of the elements, sensors, circuits, modules, processes and/or devices illustrated in FIG. 3 may be combined, divided, re-arranged, omitted, eliminated, implemented in a recursive way, and/or implemented in any other way. Further, the example vibrating wire sensor 305, the example actuator 320, the example waveform measurer 325, the example waveform modeler 330, the example initializer 331, the example modeler 332, the example output interface 335, the example telemetry module 340, the example storage 345, the example de-biaser 350, the example spectrum analyzer 355, the example transformer 360, the example decrement fitter 365, the example phase fitter 370 and/or, more generally, the example downhole assembly 300 of FIG. 3 may be implemented by hardware, software, firmware and/or any combination of hardware, software and/or firmware. Thus, for example, any or all of the example vibrating wire sensor 305, the example actuator 320, the example waveform measurer 325, the example waveform modeler 330, the example initializer 331, the example modeler 332, the example output interface 335, the example telemetry module 340, the example storage 345, the example de-biaser 350, the example spectrum analyzer 355, the example transformer 360, the example decrement fitter 365, the example phase fitter 370 and/or, more generally, the example downhole assembly 300 may be implemented by one or more circuit(s), programmable processor(s), application specific integrated circuit(s) (ASIC(s)), programmable logic device(s) (PLD(s)), field-programmable logic device(s) (FPLD(s)), field-programmable gate array(s) (FPGA(s)), etc. Further still, the downhole assembly 300 may include elements, sensors, circuits, modules, processes and/or devices instead of, or in addition to, those illustrated in FIG. 3 and/or may include more than one of any or all of the illustrated elements, sensors, circuits, modules, processes and/or devices. For example, the downhole assembly 300 may include a fluid density module (not shown) to take measurements of the fluid 310 from which the density ρ of the fluid 310 can be estimated and/or computed by the fluid density module and/or by a surface assembly, such as the example surface assemblies 27 and 27a.

Figure 4:
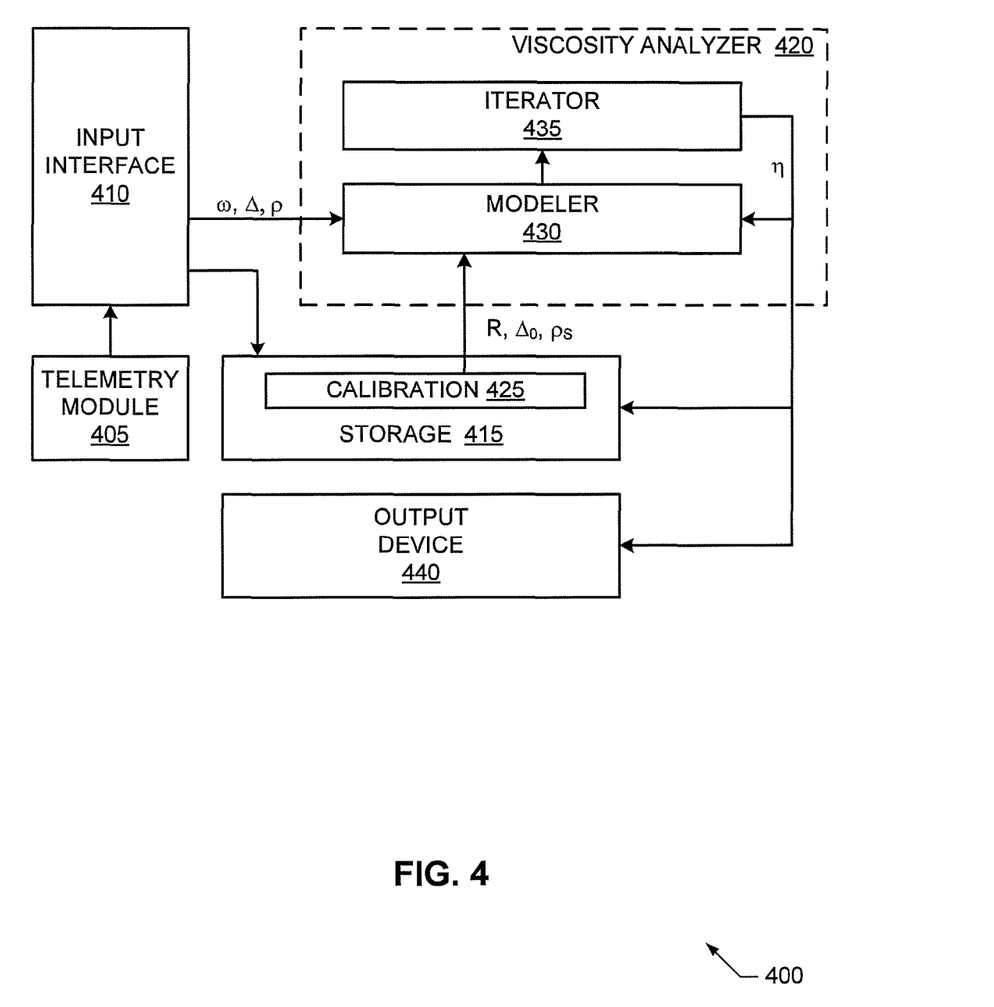
FIG. 4 illustrates an example manner of implementing the example surface fluid viscosity analysis assemblies of FIGS. 1 and 2.

FIG. 4 illustrates an example manner of implementing the example surface fluid viscosity analysis assemblies 27 and 27a of FIGS. 1 and 2. While either of the example surface fluid viscosity analysis assemblies 27 and 27a may be implemented by the example of FIG. 4, for ease of discussion, the illustrated example of FIG. 4 will be referred to as surface fluid viscosity analysis assembly 400, or simply as surface assembly 400.

To receive model parameters (e.g., $\Delta$ and $\omega$)) that represent the measured vibrations of a wire vibrating in a fluid flow, the example downhole assembly 400 of FIG. 4 includes any type of telemetry module 405, and any number and/or type(s) of input interface(s), one of which is designated at reference numeral 410. When computed model parameters are received at the input interface 410 via the example telemetry module 405, the example input interface 410 of FIG. 4 stores the received model parameters in any number and/or type(s) of memory(-ies), memory device(s), storage and/or storage device(s) 415. If a measured induced voltage waveform D(t) is received via the telemetry module 405, the waveform V(t) is likewise stored in the storage 415.

To determine the viscosity 77 of the fluid 310 (FIG. 3), the example surface fluid viscosity analysis assembly 400 of FIG. 4 includes a viscosity analyzer 420. The example viscosity analyzer 420 of FIG. 4 iteratively computes outputs of a non-linear fluid viscosity modeling equation g( ) for different estimates of the viscosity η to compute, estimate and/or otherwise iteratively solve for the viscosity η. The non-linear fluid viscosity modeling equation g( ) iterated by the example viscosity analyzer 420 is defined by the model parameters Δ and ω computed by and received from the downhole assembly 26, 26a, 300, pre-computed and/or pre-measured calibration parameters 425 for the vibrating wire sensor 305, and a measured and/or computed density ρ of the fluid 310. The density ρ of the fluid 310 of FIG. 4 may be measured by a downhole tool module and/or assembly using any number and/or type(s) of method(s), device(s), and/or algorithm(s) and is received at the surface assembly 400 via the example telemetry module 405. Additionally or alternatively, the surface assembly 400 of FIG. 4 may include a density analyzer (not shown) that estimates and/or computes the fluid density ρ based on measurements taken by a downhole tool. The example calibration parameters 425 are determined prior to the downhole assemblies 26, 26a and/or 300 being placed within the wellbore 14. Example calibration parameters 425 include, but need not be limited to, the radius R of the wire 306, the internal damping factor $\Delta_0$ of the wire 306 and the density $\rho_s$ of the wire 306.

The example viscosity analyzer 420 of FIG. 4 stores the computed and/or estimated viscosity η in the example storage 415, and/or outputs the computed and/or estimated viscosity η via any number and/or type(s) of output devices, one of which is designated at reference numeral 440. Example output devices 440 include, but are not limited to, a display, a screen, a printer and/or a terminal. Moreover, the example output device 440 may be used to provide the determined viscosity η to another surface device and/or assembly (not shown) that directs formation evaluation.

To compute values of the fluid viscosity modeling equation g( ), the example viscosity analyzer 420 of FIG. 4 includes a modeller 430. The example modeller 430 of FIG. 4 computes values of a non-linear modeling equation g( ) defined by the following mathematical expression $$g(\omega, \Delta, R, \Delta_0, \rho_s, \rho, \eta) = \Delta - \frac{(\rho/\rho_s)k' + 2\Delta_0}{2[1 + (\rho/\rho_s)k]}, \quad \text{EQN (17)}$$

where k and k' are defined by the mathematical expressions of EQNS (3) through (6).

To solve for the viscosity η, the example viscosity analyzer 420 of FIG. 4 includes an iterator 435. The example iterator 435 of FIG. 4 computes, iterates and/or otherwise solves for the viscosity value η such that the value of EQN (17) is as close to zero as possible. In some examples, the example iterator 435 uses Newton-Raphson iterations to solve for the viscosity η. Given a current estimated value $\eta_n$ of the viscos ity η, the iterator 435 computes an updated estimated value $\eta_{n+1}$ of the viscosity η using the following expression $$\eta_{n+1} = \eta_n - \frac{g(\omega, \Delta, R, \Delta_0, \rho_s, \rho, \eta_n)}{g'(\omega, \Delta, R, \Delta_0, \rho_s, \eta_n)}, \quad \text{EQN (18)}$$

where $$g'(\omega, \Delta, R, \Delta_0, \rho_s, \rho, \eta_n) = \left.\frac{\partial}{\partial \eta}g(\omega, \Delta, R, \Delta_0, \rho_s, \rho, \eta)\right|_{\eta=\eta_n}. \quad \text{EQN (19)}$$

Because the example nonlinear function $g(\omega,\Delta,R,\Delta_0,\rho_s,\rho,\eta)$ is well behaved with respect to η (i.e., it has a single zero crossing), iterations can start with an initial estimated viscosity $\eta_0$ of 1 centipoises (cP). Alternatively, one can approximate the viscosity η as a constant times the square of the decrement Δ and use it as an initial starting point $\eta_0$ for iterations of the viscosity modeling equation g( ). Convergence of the example iteration expressed by EQNS (18) and (19) will typically occur in less than 10 iterations.

While an example manner of implementing the example surface fluid viscosity analysis assemblies 27 and 27a of FIGS. 1 and 2 has been illustrated in FIG. 4, one or more of the elements, sensors, circuits, modules, processes and/or devices illustrated in FIG. 4 may be combined, divided, rearranged, omitted, eliminated, implemented in a recursive way, and/or implemented in any other way. Further, the example telemetry module 405, the example input interface 410, the example storage 415, the example viscosity analyzer 420, the example modeler 430, the example iterator 435, the example output device 440 and/or, more generally, the example surface assembly 400 of FIG. 4 may be implemented by hardware, software, firmware and/or any combination of hardware, software and/or firmware. Thus, for example, any or all of the example telemetry module 405, the example input interface 410, the example storage 415, the example viscosity analyzer 420, the example modeler 430, the example iterator 435, the example output device 440 and/or, more generally, the example surface assembly 400 may be implemented by one or more circuit(s), programmable processor(s), ASIC(s), PLD(s), FPLD(s), FPGA(s), etc. Further still, the surface assembly 400 may include elements, sensors, circuits, modules, processes and/or devices instead of, or in addition to, those illustrated in FIG. 4 and/or may include more than one of any or all of the illustrated elements, sensors, circuits, modules, processes and/or devices.

Figure 5:
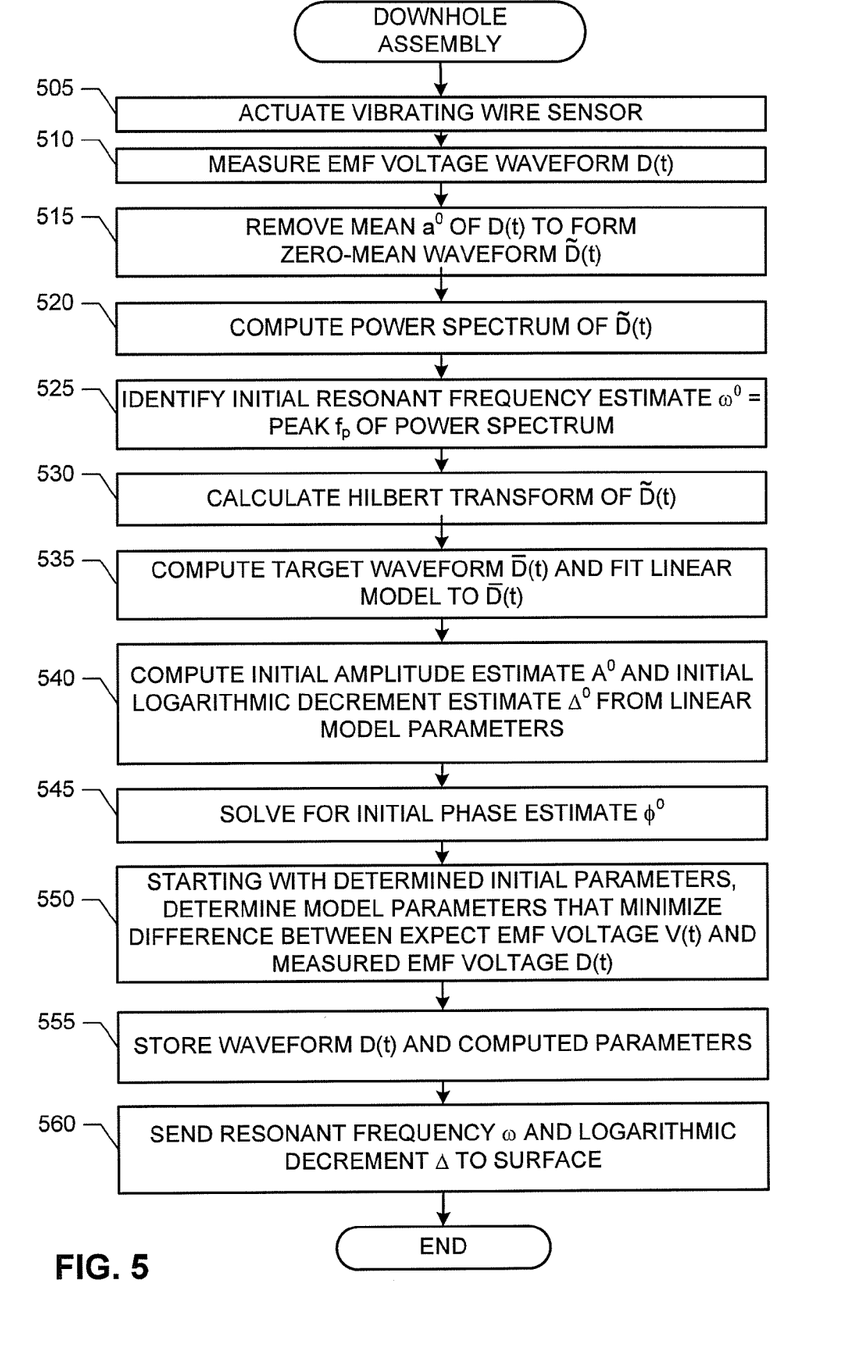
FIG. 5 illustrates an example process that may be carried out to implement the example downhole fluid viscosity analysis assemblies of FIGS. 1-3.
Figure 6:
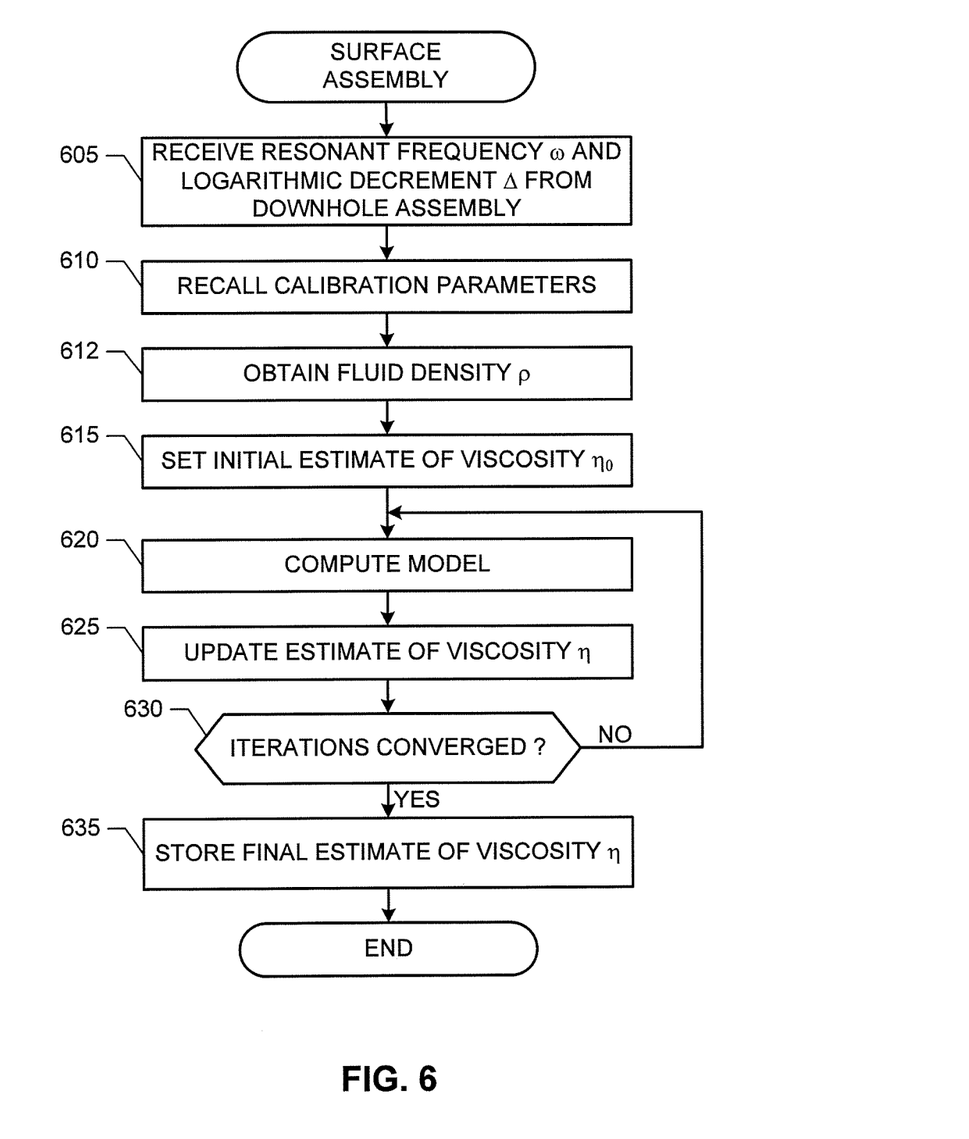
FIG. 6 illustrates an example process that may be carried out to implement the example surface fluid viscosity analysis assemblies of FIGS. 1-2 and 4.

FIG. 5 is a flowchart representative of an example process that may be carried out to implement the example downhole fluid viscosity analysis assemblies 26, 26a and 300 of FIGS. 1-3. FIG. 6 is a flowchart representative of an example process that may be carried out to implement the example surface fluid viscosity analysis assemblies 27, 27a and 400 of FIGS. 1, 2 and 4. The example processes of FIGS. 5 and 6 may be carried out by a processor, a controller and/or any other suitable processing device. For example, the example processes of FIGS. 5 and 6 may be embodied in coded instructions stored on an article of manufacture such as any tangible computer-readable and/or computer-accessible medium. Example tangible computer-readable medium include, but are not limited to, a flash memory, a compact disc (CD), a digital versatile disc (DVD), a floppy disk, a read-only memory (ROM), a random-access memory (RAM), a programmable ROM (PROM), an electronically-programmable ROM (EPROM), and/or an electronically-erasable PROM (EEPROM), an optical storage disk, an optical storage device, magnetic storage disk, a magnetic storage device, and/or any other tangible medium which can be used to store and/or carry program code and/or instructions in the form of machine-accessible and/or machine-readable instructions or data structures, and which can be accessed by a processor, a general-purpose or special-purpose computer, or other machine with a processor (e.g., the example processor platform P100 discussed below in connection with FIG. 7). Combinations of the above are also included within the scope of computer-readable media. Machine-readable instructions comprise, for example, instructions and/or data that cause a processor, a general-purpose computer, special-purpose computer, or a special-purpose processing machine to implement one or more particular processes. Alternatively, some or all of the example processes of FIGS. 5 and 6 may be implemented using any combination(s) of ASIC(s), PLD(s), FPLD(s), FPGA(s), discrete logic, hardware, firmware, etc. Also, some or all of the example processes of FIGS. 5 and 6 may instead be implemented manually or as any combination of any of the foregoing techniques, for example, any combination of firmware, software, discrete logic and/or hardware. Further, many other methods of implementing the example operations of FIGS. 5 and 6 may be employed. For example, the order of execution of the blocks may be changed, and/or one or more of the blocks described may be changed, eliminated, subdivided, or combined. Additionally, any or all of the example processes of FIGS. 5 and 6 may be carried out sequentially and/or carried out in parallel by, for example, separate processing threads, processors, devices, discrete logic, circuits, etc.

The example process of FIG. 5 begins with the example actuator 320 actuating and/or causing a deflection of the wire 306 (block 505), and the example waveform measurer 325 measures over time the voltage waveform D(t) induced across the wire 306 by the vibration of the wire within the fluid 310 (block 510). The example de-biaser 350 computes the initial estimated average $a^0$ of the measured waveform D(t) and subtracts the average $a^0$ from the measured waveform D(t) to form the zero-mean waveform $\tilde{D}(t)$ as shown in EQN (11) (block 515).

The example spectrum analyzer 355 computes the power spectrum of the zero-mean waveform $\tilde{D}(t)$ (block 520) and identifies the frequency $f_p$ corresponding to the peak of the computed power spectrum (block 525). The initial resonant frequency estimate $\omega^0$ is computed as $\omega^0 = 2\pi f_p$.

The example transformer 360 computes the Hilbert Transform of the zero-mean waveform $\tilde{D}(t)$ (block 530). The transformer 360 computes the target waveform $\overline{D}(t)$ using, for example, EQN (12) and the example decrement fitter 365 selects the unknown parameters c and d of a linear model to reduce a difference between the linear model and the target waveform as, for example, shown in EQN (13) (block 535). The decrement fitter 365 computes the initial estimated logarithmic decrement $\Delta^0$ and the amplitude $A^0$ from the parameters c and d as shown in EQN (14) and (15), respectively (block 540).

The example phase fitter 370 solves for the initial estimated phase $\phi^0$ as, for example, described above in connection with EQN (16) (block 545). Starting with the initial estimated model parameters $A^0, a^0, b^0, \Delta^0, \phi^0$, and $\omega^0$ ($A_3^0$ ad $f_3^0$ for the dual-exponent model) the example modeler 332 computes, determines, updates and/or iterates the model parameters A, a, b, $\Delta$, $\phi$, and $\omega$ ($A_3$ and $\phi_3$ for the dual-exponent model) to minimize a difference between the measured D(t) and the expected V(t) (block 550).

The waveform modeler 330 stores the measured waveform D(t) and the computed model parameters in the storage 345 (block 555), and the output interface 335 sends at least the computed model parameters $\Delta$ and $\omega$ to a surface location via the telemetry module 340 (block 560). Control then exits from the example process of FIG. 5.

The example process of FIG. 6 begins with the example telemetry module 405 (FIG. 4) receiving the computed model parameters $\Delta$ and $\omega$ from a downhole tool (block 605). The example modeler 430 recalls the calibration parameters R, $\Delta_0$ and $\rho_s$ from the storage 425 (block 610). The example telemetry module 405 receives the fluid density $\rho$ from the same or a different downhole tool (block 612). Additionally or alternatively, the fluid density $\rho$ can be obtained by computing and/or estimating the density $\rho$ based on measurements taken by a downhole tool. The example iterator 435 selects an initial estimate $\eta_0$ of the viscosity $\eta$ of the fluid 310 (block 615).

Based on the received parameters $\Delta$ and $\omega$ received from the downhole tool, the recalled calibration parameters and the initial estimate of the viscosity $\eta$, the example modeler 430 computes an output of the non-linear fluid viscosity modeling equation g( ) defined by EQN (17) (block 620). Based on the output of the fluid viscosity modeling equation g( ) computed by the modeler 430, the example iterator 435 computes an updated estimate $\eta_{n+1}$ of the viscosity $\eta$ using, for example, EQNS (18) and (19) (block 625).

If the estimate of the viscosity $\eta$ has not converged (block 630), control returns to block 620 to compute another output of the fluid viscosity modeling equation g( ). If the estimate of the viscosity $\eta$ has converged (block 630), the viscosity analyzer 420 stores the estimated viscosity $\eta$ in the storage 415 and/or outputs the estimated viscosity $\eta$ via the output device 440 (block 635). Control then exits from the example process of FIG. 6.

Figure 7:
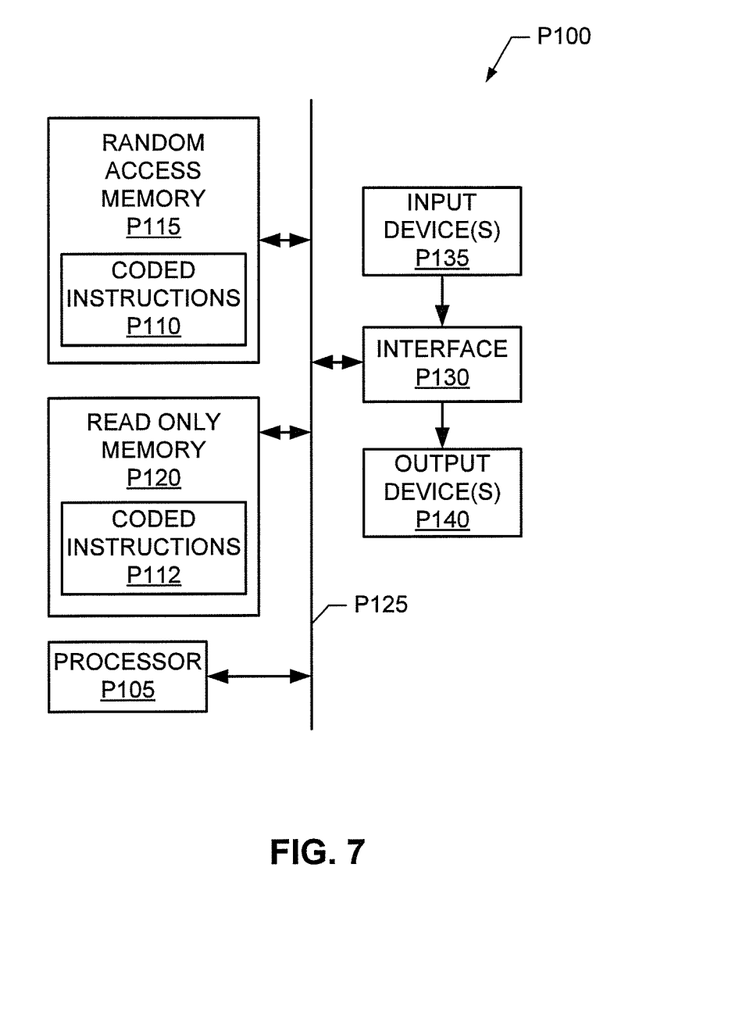
FIG. 7 is a schematic illustration of an example processor platform that may be used and/or programmed to carry out the example processes of FIGS. 5 and 6, and/or to implement any of all of the methods, apparatus and articles of manufacture disclosed herein.

FIG. 7 is a schematic diagram of an example processor platform P100 that may be used and/or programmed to implement the example fluid viscosity analysis assemblies 26, 26a, 27, 27a, 300 and 400 described herein. For example, the processor platform P100 can be implemented by one or more general-purpose processors, processor cores, microcontrollers, etc.

The processor platform P100 of the example of FIG. 7 includes at least one general-purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example processes of FIGS. 5 and 6 to implement the example methods, apparatus and articles of manufacture described herein.

The processor P105 is in communication with the main memory (including a ROM P120 and/or the RAM P115) via a bus P125. The RAM P115 may be implemented by dynamic random-access memory (DRAM), synchronous dynamic random-access memory (SDRAM), and/or any other type of RAM device, and ROM may be implemented by flash memory and/or any other desired type of memory device. Access to the memory P115 and the memory P120 may be controlled by a memory controller (not shown). The memory P115, P120 may be used to implement the example storage 345 and 415.

The processor platform P100 also includes an interface circuit P130. The interface circuit P130 may be implemented by any type of interface standard, such as an external memory interface, serial port, general-purpose input/output, etc. One or more input devices P135 and one or more output devices P140 are connected to the interface circuit P130. The example output device P140 may be used to, for example, implement the example telemetry module 340. The example input device P135 may be used to, for example, implement the example telemetry module 405.

Although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. An apparatus comprising:
   a downhole assembly including:
      a sensor to measure a waveform representative of a motion of a wire vibrating within a fluid at a downhole location in a wellbore;
      a waveform modeler to compute a model parameter from the measured waveform; and
      a first telemetry module to transmit the computed model parameter to a surface location; and
   a surface assembly including:
      a second telemetry module to receive the computed model parameter from the downhole assembly; and
      a viscosity analyzer to estimate a viscosity of the fluid from the computed model parameter.

2. The apparatus as defined in claim 1, wherein the waveform modeler is to compute the model parameter by solving a first minimization problem, and the viscosity analyzer is to estimate the viscosity by solving a second minimization problem.

3. The apparatus as defined in claim 1, wherein the computed model parameter comprises at least one of a logarithmic decrement damping factor or a resonant frequency of the vibrating wire.

4. The apparatus as defined in claim 1, wherein the waveform modeler comprises:
   a transformer to compute a Hilbert transform of the measured waveform and to compute a target waveform based on the Hilbert transform and the measured waveform; and
   a decrement filter to fit a linear model having a slope coefficient and a constant to the computed target waveform and to compute the model parameter from the slope coefficient of the linear model.

5. The apparatus as defined in claim 1, wherein the waveform modeler comprises a spectrum analyzer to compute a power spectrum of the measured waveform and to identify a peak of the computed power spectrum, wherein the model parameter represents the peak of the computed power spectrum.

6. The apparatus as defined in claim 1, wherein the waveform modeler comprises a modeler to update the computed model parameter to reduce a difference between the measured waveform and an expected waveform.

7. The apparatus as defined in claim 1, wherein the viscosity analyzer comprises:
   a modeler to compute output values of a nonlinear function that characterizes the vibrating wire, the nonlinear function defined by the computed model parameter and at least one calibration parameter; and
   an iterator to estimate the viscosity by identifying a zero point of the nonlinear function based on the computed output values.

8. The apparatus as defined in claim 7, wherein the iterator is to identify the zero point by:
   selecting a first estimated value of the viscosity; and
   calculating a second estimated value of the viscosity from the first estimated viscosity value using a Newton-Raphson iteration.

9. A method comprising:
   actuating a wire sensor within a fluid;
   measuring a waveform representative of a vibration of the wire sensor within the fluid;
   computing a wire vibration model parameter comprising at least one of a resonant frequency or a logarithmic decrement damping factor from the measured waveform; and
   estimating a viscosity of the fluid from the computed model parameter,
   said method further comprising:
      computing a Hilbert transform of the measured waveform;
      computing a target waveform based on the Hilbert transform and the measured waveform;
      fitting a linear model having a slope coefficient and a constant to the computed target waveform; and
      computing the model parameter based on the slope coefficient of the linear model,
   wherein the method is performed with an apparatus capable of processing measurements of wires vibrating in fluids.

10. The method as defined in claim 9, wherein the wire vibration model parameter is computed by solving a first minimization problem, and the viscosity of the fluid is estimated by solving a second minimization problem.

11. The method as defined in claim 9, further comprising estimating the viscosity of the fluid by identifying a zero point of a nonlinear function defined by the computed model parameter and at least one calibration parameter.

12. A method comprising:
    actuating a wire sensor within a fluid;
    measuring a waveform representative of a vibration of the wire sensor within the fluid;
    computing a wire vibration model parameter comprising at least one of a resonant frequency or a logarithmic decrement damping factor from the measured waveform; and
    estimating a viscosity of the fluid from the computed model parameter,
    said method further comprising:
       computing a power spectrum of the measured waveform; and
       identifying a peak of the computed power spectrum, wherein the model parameter represents the peak of the computed power spectrum,
    wherein the method is performed with an apparatus capable of processing measurements of wires vibrating in fluids.

13. The method as defined in claim 12, wherein the wire vibration model parameter is computed by solving a first minimization problem, and the viscosity of the fluid is estimated by solving a second minimization problem.

14. The method as defined in claim 12, further comprising estimating the viscosity of the fluid by identifying a zero point of a nonlinear function defined by the computed model parameter and at least one calibration parameter.

15. A method comprising:
    actuating a wire sensor within a fluid;
    measuring a waveform representative of a vibration of the wire sensor within the fluid;

computing a wire vibration model parameter comprising at least one of a resonant frequency or a logarithmic decrement damping factor from the measured waveform; and estimating a viscosity of the fluid from the computed model parameter, said method further comprising:
  selecting a first estimated value of the viscosity; and
  performing a Newton-Raphson iteration to form a second estimated value of the viscosity,
wherein the method is performed with an apparatus capable of processing measurements of wires vibrating in fluids.

16. The method as defined in claim 15, wherein the wire vibration model parameter is computed by solving a first minimization problem, and the viscosity of the fluid is estimated by solving a second minimization problem.

17. The method as defined in claim 15, further comprising estimating the viscosity of the fluid by identifying a zero point of a nonlinear function defined by the computed model parameter and at least one calibration parameter.

18. An apparatus for use at a downhole location of a wellbore, comprising:
  an actuator to actuate a wire within a fluid at the downhole location of the wellbore;
  a measurer to measure a waveform representative of a vibration of the wire within the fluid;
  a transformer to compute a Hilbert transform of the measured waveform and to compute a target waveform based on the Hilbert transform and the measured waveform;
  a decrement filter to fit a linear model having a slope coefficient and a constant to the computed target waveform and to compute a logarithmic decrement damping factor from the slope coefficient of the linear model; and
  a telemetry module to send the computed logarithmic decrement damping factor to a surface location.

19. The apparatus as defined in claim 18, wherein computing the logarithmic decrement damping factor comprises computing a ratio of the slope coefficient and a resonant frequency of the wire within the fluid.

20. The apparatus as defined in claim 18, further comprising:
  a spectrum analyzer to compute a power spectrum of the measured waveform and to identify a peak of the computed power spectrum at a resonant frequency of the wire within the fluid, wherein the telemetry module is to send the resonant frequency to the surface location.

21. The apparatus as defined in claim 18, further comprising a de-biaser to compute an average of the measured waveform and to subtract the average from the measured waveform to form a zero-mean measured waveform, wherein the transformer is to compute the Hilbert transform of the zero-mean measured waveform.

22. The apparatus as defined in claim 15, further comprising a modeler to update the computed logarithmic decrement damping factor to reduce a difference between the measured waveform and an expected waveform.

23. A method comprising:
  actuating a wire within a fluid at a downhole location within a wellbore;
  measuring a waveform representative of a vibration of the wire within the fluid;
  computing a Hilbert transform of the measured waveform;
  computing a target waveform based on the Hilbert transform and the measured waveform;
  fitting a linear model having a slope coefficient and a constant to the computed target waveform;
  computing a logarithmic decrement damping factor based on the slope coefficient of the linear model; and
  sending the computed logarithmic decrement damping factor to a surface location,
wherein the method is performed with an apparatus capable of processing measurements of wires vibrating in fluids.

24. The method as defined in claim 23, wherein computing the logarithmic decrement damping factor comprises computing a ratio of the slope coefficient and a resonant frequency of the wire within the fluid.

25. The method as defined in claim 23, further comprising:
  computing a power spectrum of the measured waveform;
  identifying a peak of the computed power spectrum at a resonant frequency of the wire within the fluid; and
  sending the resonant frequency to the surface location.

26. The method as defined in claim 23, further comprising:
  computing an average of the measured waveform; and
  subtracting the average from the measured waveform to form a zero-mean measured waveform, wherein the Hilbert transform is computed on the zero-mean measured waveform.

27. The method as defined in claim 23, further comprising updating the computed logarithmic decrement damping factor to reduce a difference between the measured waveform and an expected waveform.

28. The method as defined in claim 27, wherein updating the computed logarithmic decrement damping factor to reduce a difference between the measured waveform and the expected waveform comprises a Levenberg-Marquardt iteration.

29. The method as defined in claim 23, further comprising:
  estimating a viscosity of the fluid based on the computed logarithmic decrement damping factor; and
  determining a parameter of a formation evaluation test based on the estimated viscosity.

30. The method as defined in claim 29, wherein estimating the viscosity comprises:
  computing a square of the computed logarithmic decrement damping factor; and
  computing a product of the square and a constant.

31. The method as defined in claim 29, wherein the parameter of the formation evaluation test comprises a draw down rate.

32. A method comprising:
  receiving at a surface location a logarithmic decrement damping factor for a wire vibrating within a fluid at a downhole location within a wellbore;
  receiving at the surface location from the downhole location a resonant frequency of the vibrating wire within the fluid within the wellbore at the downhole location; and
  estimating a viscosity of the fluid based on the received logarithmic decrement damping factor and the received resonant frequency,
wherein estimating the viscosity of the fluid comprises identifying a zero point of a nonlinear function defined by the viscosity, the received logarithmic decrement damping factor, the received resonant frequency and a calibration parameter,
wherein the nonlinear function comprises a difference between the received logarithmic decrement damping factor and a modeled logarithmic decrement damping factor computed using the viscosity, the received resonant frequency and the calibration parameter, and wherein the method is performed with an apparatus capable of processing measurements of wires vibrating in fluids.

33. A method comprising:

receiving at a surface location a logarithmic decrement damping factor for a wire vibrating within a fluid at a downhole location within a wellbore;

receiving at the surface location from the downhole location a resonant frequency of the vibrating wire within the fluid within the wellbore at the downhole location; and estimating a viscosity of the fluid based on the received logarithmic decrement damping factor and the received resonant frequency, wherein estimating the viscosity of the fluid comprises:
selecting a first estimated value of the viscosity; and
performing a Newton-Raphson iteration to compute a second estimated value of the viscosity, and wherein the method is performed with an apparatus capable of processing measurements of wires vibrating in fluids.

34. The method as defined in claim 33, wherein estimating the viscosity of the fluid comprises identifying a zero point of a nonlinear function defined by the viscosity, the received logarithmic decrement damping factor, the received resonant frequency and a calibration parameter.

* * * * *